United States Patent
Narendranath et al.

(10) Patent No.: US 10,900,016 B2
(45) Date of Patent: Jan. 26, 2021

(54) METHOD AND SYSTEM FOR PROPAGATING A MICROORGANISM

(71) Applicant: POET Research, Inc., Sioux Falls, SD (US)

(72) Inventors: Neelakantam V. Narendranath, Sioux Falls, SD (US); Stephen M. Lewis, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 44 days.

(21) Appl. No.: 15/736,938

(22) PCT Filed: Jun. 17, 2016

(86) PCT No.: PCT/US2016/037990
§ 371 (c)(1),
(2) Date: Dec. 15, 2017

(87) PCT Pub. No.: WO2016/205596
PCT Pub. Date: Dec. 22, 2016

(65) Prior Publication Data
US 2018/0171285 A1    Jun. 21, 2018

Related U.S. Application Data (60) Provisional application No. 62/180,892, filed on Jun. 17, 2015.

(51) Int. Cl.
*C12N 1/32* (2006.01)
*C12N 1/18* (2006.01)
*C12N 1/16* (2006.01)
*C12M 1/00* (2006.01)

(52) U.S. Cl.
CPC .............. *C12N 1/32* (2013.01); *C12M 29/24* (2013.01); *C12N 1/16* (2013.01); *C12N 1/18* (2013.01)

(58) Field of Classification Search
CPC ........ A23K 10/38; A23K 10/12; A23K 50/80; A23K 10/37; C12P 7/649; C12P 7/16; C12P 2203/00; C12P 7/18; C12P 7/62; C12P 7/06; C12P 7/10; C12P 7/04; C12P 13/04; C12P 21/06; C12P 2201/00; C12P 7/065; C12P 7/625; C12P 7/6418; C12P 7/6463; C12P 19/02; C12P 19/14; C12P 1/02; C12P 7/14; C12P 7/12; C12P 7/08; C12P 17/04; Y02E 50/17; Y02E 50/13; Y02E 50/10; Y02E 50/16; Y02P 60/873; Y02P 30/20; Y02P 20/57; Y02P 20/59; Y02P 70/34; C12N 1/14; C12N 1/18; C12N 9/18; C12N 15/00; C12N 1/20; C12N 1/36; C12N 15/1096; C12N 15/81; C12N 1/16; C12N 1/22; C12N 1/32; C12N 9/0006; C12N 9/0008; C12N 1/24; C12N 1/38; C12N 15/52; C12N 9/2414; A23L 33/12; A23L 33/195; A23L 7/104; A23L 7/198; A23L 7/20; B01D 11/0492; B01D 21/26; B01D 21/262; B01D 3/002; B01D 1/28; B01D 3/007; B01D 3/143; C02F 1/722; C02F 1/76; C02F 1/78; C02F 2103/32; C02F 3/34; C07C 29/86; C07C 31/12; C07C 29/76; C07C 29/80; C08H 8/00; C11B 13/00; C11B 1/025; C12F 3/10; C12M 1/00; C12M 21/12; C12M 45/04; C12M 45/09; C12M 29/24; C12M 25/00; C12M 35/04; C12M 41/12; C12M 27/00; C12M 21/18; C12R 1/01; C12R 1/865; G06Q 99/00; Y02A 40/818; Y02W 10/37; Y02W 30/74; Y02W 30/648; C12Q 1/40; C12Q 1/48; C12Q 1/527; C13K 1/02; D21B 1/12; D21C 11/0007; D21C 1/02; D21C 5/02; D21D 99/00; C07D 307/50; C12Y 302/01001; C12Y 302/01003
See application file for complete search history.

(56) References Cited

U.S. PATENT DOCUMENTS

| | | | | |
|---|---|---|---|---|
| 5,177,008 A | * | 1/1993 | Kampen .................. | C12F 3/10 435/139 |
| 5,503,750 A | * | 4/1996 | Russo, Jr. .............. | B01D 61/58 210/259 |
| 8,183,022 B2 | | 5/2012 | Steiner | |
| 8,481,295 B2 | * | 7/2013 | van Leeuwen .......... | C12N 1/14 435/171 |
| 8,697,404 B2 | * | 4/2014 | Anton ...................... | C12N 9/18 435/134 |
| 8,722,383 B2 | * | 5/2014 | Smith ....................... | C12R 1/01 435/135 |
| 9,029,126 B2 | * | 5/2015 | Bleyer ..................... | B01D 3/14 435/262 |
| 9,040,263 B2 | * | 5/2015 | Anton ...................... | C12P 7/16 435/134 |
| 9,175,315 B2 | * | 11/2015 | Anton .................... | B01D 3/002 |
| 9,752,164 B2 | * | 9/2017 | Razavi-Shirazi ......... | C12P 7/14 |
| 9,994,872 B2 | * | 6/2018 | Lennartsson ........... | C12P 7/065 |

(Continued)

FOREIGN PATENT DOCUMENTS

WO    2014160184    10/2014

OTHER PUBLICATIONS

Samul et al "Impurities of crude glycerol and their effect on metabolite production", Ann Microbiol. 2014; 64(3):pp. 891-898. (Year: 2014).*

(Continued)

*Primary Examiner* — Deborah K Ware
(74) *Attorney, Agent, or Firm* — Kagan Binder, PLLC (57) ABSTRACT

Disclosed are methods and systems for propagating microorganisms such as yeast using a carbon source that includes glycerol and a nutrient source that includes a stillage component.

11 Claims, 4 Drawing Sheets

(56) References Cited

U.S. PATENT DOCUMENTS

| | | | | |
|---|---|---|---|---|
| 2009/0291469 | A1* | 11/2009 | David | C12N 1/18 435/69.1 |
| 2010/0041116 | A1* | 2/2010 | Lewis | C12P 7/06 435/161 |
| 2010/0196994 | A1* | 8/2010 | van Leeuwen | C02F 3/34 435/256.1 |
| 2010/0279354 | A1* | 11/2010 | de Crecy | C12P 7/6463 435/71.1 |
| 2010/0317076 | A1 | 12/2010 | Rymowicz | |
| 2011/0269185 | A1* | 11/2011 | David | C12N 1/18 435/69.1 |
| 2011/0269201 | A1* | 11/2011 | Gray | C12N 9/0006 435/161 |
| 2012/0156738 | A1* | 6/2012 | Anton | B01D 3/002 435/135 |
| 2012/0208246 | A1* | 8/2012 | Anton | C12P 7/16 435/134 |
| 2012/0301933 | A1* | 11/2012 | Smith | C12P 7/625 435/135 |
| 2012/0322117 | A1* | 12/2012 | Anton | C12N 9/18 435/157 |
| 2014/0142352 | A1* | 5/2014 | Dauner | C12P 7/16 568/913 |
| 2014/0178529 | A1* | 6/2014 | Anton | C12N 9/18 426/53 |
| 2014/0206058 | A1 | 7/2014 | Tewalt et al. | |
| 2014/0315258 | A1* | 10/2014 | Nguyen | C12P 19/02 435/99 |
| 2015/0004672 | A1* | 1/2015 | de Crecy, Jr. | C12P 7/6463 435/245 |
| 2016/0115503 | A1* | 4/2016 | Bleyer | C12N 1/005 530/350 |
| 2016/0312247 | A1* | 10/2016 | Lennartsson | C12P 7/065 |
| 2018/0171285 | A1* | 6/2018 | Narendranath | C12M 29/24 |
| 2018/0245109 | A1* | 8/2018 | Jeffries | C12P 7/649 |

OTHER PUBLICATIONS

Granada, "Produciton of Naturally Occurring Carboxylic Acids from Anaerobic Dig. of Org. Materials", Earth Energy Renewables, Washington DC, Jul. 11, 2017, pp. 1-28. (Year: 2017).*

Wood et al "Quantification of Physical and Chemical Prop., and Identif. of Potentially Valuable Componenets from Fuel Ethanol Process Streams", Cereal Chem. 90(1):70-79 (Year: 2013).*

Ferreira et al "Production of Ethanol and Biomass from Thin Stillage Using Food-Grade Zygomycetes and Ascomycetes Filamentous Fungi", Energies 2014, 7, pp. 3872-3885. (Year: 2014).*

Wood et al, "Quantification of Phy. and Chem.Properties and Ident. of Potentially Valuable Components from Fuel Ethanol Process Streams", Cereal Chem., vol. 90(1), pp. 70-79, 2013. (Year: 2013).*

Thompson, et al. "Characterization of Crude Glycerol From Biodiesel Production From Multiple Feedstocks," Applied Engineering in Agriculture, 22(2), pp. 261-265, (2006).

Gonzalez, et al., "Production of ethanol from thin stillage by metabolically engineered *Escherichia coli*", Biotechnology Letter 32, pp. 405-411 (2010).

Mu, et al., "Microbial production of 1,3-propanediol by Klebsiella pneumoniae using crude glycerol from biodiesel preparations", Biotechnology Letters, 28, pp. 1755-1759 (2006).

REG Glycerin Fact Sheet, Renewable Energy Group, Inc., 2 pages (2014).

Papanikolaou, et al., "Lipid production of Yarrowia lipolytica growing on industrial glycerol in a single-stage continuous culture," Bioresource Technology, 82, pp. 43-49 (2002).

Yang et al., "Value-added uses for crude glycerol-a byproduct of biodiesel production", Biotechnology of Biofuels, 5(13), 10 pages, (2012).

Written Opinion and International Search Report for International Application No. PCT/US2016/037990, dated Sep. 7, 2016, 9 pages.

Johnson, et al., "The Glycerin Glut: Options for the Value-Added Conversion of Crude Gycerol Resulting from Biodiesel Production", Environmental Progress, 26(4), 338-348 (2007).

* cited by examiner

METHOD AND SYSTEM FOR PROPAGATING A MICROORGANISM

CROSS-REFERENCE TO RELATED APPLICATIONS & PRIORITY CLAIM

This application claims priority to U.S. Provisional Application No. 62/180,892 filed Jun. 17, 2015, which is herein incorporated by reference in its entirety.

BACKGROUND

Propagating microorganisms, namely to increase the quantity of the microorganisms, may be desirable when the particular microorganism is expensive or when the microorganism can be used as feed or feed supplements. Propagation, particularly yeast propagation, can be challenging. For example, some microorganisms such as *Saccharomyces cerevisiae* can be susceptible to the well-known "Crabtree effect" when grown on glucose, even under sufficiently aerated conditions, if the glucose concentration in the medium is high (e.g., exceeds 5 grams per Liter). At high glucose levels, the yeast can start to make ethanol through a fermentative pathway instead of producing more yeast through a respiration pathway (i.e., suppression of respiration by high glucose levels). To reduce or prevent the Crabtree effect, yeast manufacturers often grow yeast via a fed-batch or slow feeding process, where the carbon source (glucose) for producing yeast biomass is introduced at a rate that avoids undue ethanol production. However, fed-batch systems can be relatively expensive and challenging for ethanol manufacturers to control and manage.

There is a desire to develop methods of propagating microorganisms such as yeast using batch process protocols instead of fed-batch process protocols because batch processes can be simpler to control and more tolerant to variation in process parameters (e.g., with respect to varying levels of a carbon source and the Crabtree effect).

Further, there is a desire to use alternative, more accessible, and/or more economical components used in a propagation medium (e.g., carbon source, nutrient source, and the like).

SUMMARY

Disclosed are methods and systems of propagating a microorganism that uses glycerol as a carbon source and a stillage component as a nutrient source. For microorganisms that can use glycerol instead of or in addition to glucose for propagation, using glycerol can avoid the Crabtree effect observed with using glucose. For example, the level of glycerol can vary over a wide range (e.g., including a level corresponding to level of glucose that would induce the Crabtree effect), yet propagation via aerobic respirative pathway continues without switching to an anaerobic fermentative pathway to produce ethanol to an undue degree. Because the Crabtree effect can be avoided using glycerol, propagation can be performed using a batch process.

Using at least a portion of the stillage component as part of (or all of) a nutrient source of a propagation medium can provide results as good as, or better than those compared to a conventional nutrient source such as yeast extract. Also, using at least a portion of a stillage component in the nutrient portion of a propagation medium permits the use of a by-product from a corn-to-ethanol process.

Lower amounts of initial cell mass can also be used in propagating a microorganism such as yeast (e.g., as low as 1.0 gram of yeast per liter of medium, as low as 0.02 grams of yeast per liter of medium, or even lower).

Microorganisms that can use glycerol to propagate or ferment include some genetically modified yeast. Advantageously, using glycerol can prevent "contaminant" yeast (such as *Saccharomyces cerevisiae* that do not prefer to grow on glycerol as the carbon source) from competing with the microorganism that is targeted for propagation.

According to one aspect of the invention is disclosed a method of propagating a microorganism, the method comprising:

growing a first cell mass of the microorganism on a composition, the composition comprises a carbon source and a nutrient source, wherein the carbon source comprises glycerol and the nutrient source comprises a stillage component to propagate the first cell mass of the microorganism to form a second cell mass of the microorganism.

In another aspect of the invention is disclosed a method of propagating a microorganism comprising:

(a) combining a composition with a first cell mass of a microorganism, the composition comprising:
  (i) a carbon source comprising glycerol; and
  (ii) a nutrient source comprising a stillage component; and
(b) growing on the composition the first cell mass of the microorganism for a time period to form a second cell mass of the microorganism.

In still another aspect of the invention is disclosed a system for propagating a microorganism comprising:

(a) a propagation reactor vessel, wherein the propagation reactor vessel contains a composition comprising:
  (i) a carbon source comprising glycerol;
  (ii) a nutrient source comprising a stillage component; and
  (iii) a first cell mass of microorganism; wherein the microorganism can use the composition as a feed source and wherein the propagation reactor vessel is configured for growth of the first cell mass of microorganism to form a second cell mass of microorganism; and
(b) an aerator coupled to the propagation reactor vessel.

DETAILED DESCRIPTION

Figure 1:
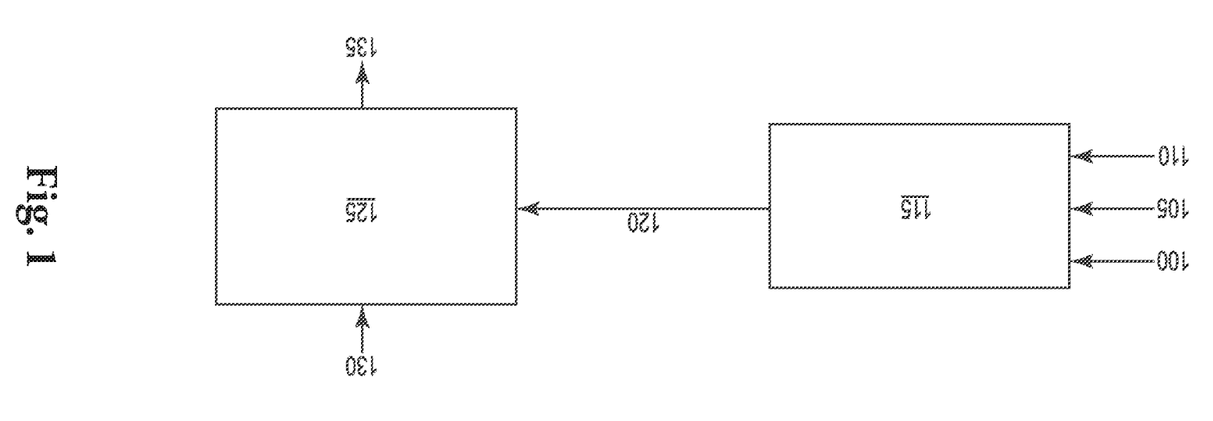
FIG. 1 shows a flow diagram of a propagation system according to an embodiment of the invention.

Disclosed are methods and systems for propagating a microorganism such as yeast. For example, propagation can be used to reproduce an initial (e.g., "starter") population of a microorganism so as to generate a larger population of the microorganism that is sufficient for use in fermentation and to make a fermentation product. An exemplary process flow diagram is illustrated in FIG. 1. The disclosed methods and systems may also be used to generate or increase the amount of the microorganism population, which may be collected and dried for use as a nutritional or feed supplement or for other purposes.

As shown in FIG. 1, a first cell mass of the microorganism 100, a carbon source 105, and a nutrient source 110 are combined in a propagation system 115 so that the first cell mass 100 can reproduce and form a second cell mass 120. The second cell mass 120 can then be used in a fermentation system 125 to convert one or more monosaccharides (e.g., from a pretreated lignocellulosic biomass) 130 into a fermentation product 135 that includes a biochemical such as a biofuel (e.g., ethanol, butanol, and the like).

Microorganisms that can convert one or more monosaccharides into a biochemical are well known and include, e.g., bacteria and/or fungi such as yeast. The product biochemicals can vary depending on the conditions that are provided. In many embodiments, the biochemicals include biofuels such as ethanol, butanol, and the like. In some embodiments, the microorganism includes one or more ethanologenic microorganisms referred to as "ethanologens". As used herein, an "ethanologen" refers to a microorganism that can convert one or more monosaccharides (e.g., glucose and the like) into at least ethanol.

The microorganism to be propagated can be prokaryotic (e.g. bacteria) and eukaryotic (e.g. yeast, fungi and algae) microorganisms. Exemplary bacterial microorganisms include the genera *Escherichia, Bacillus, Klebsiella, Lactobacillus, Lactococcus,* and the like. Exemplary algae include the genus *Chlorella, Thraustochytriu, Schizochytrium, Crypthecodinium,* and the like. In some embodiments, the algae are heterotrophic algae.

Exemplary yeast and fungus include the genus of, *Aspergillus, Candida, Pichia,* (Hansenula), *Phanerochaete, Kloeckera* (Hanseniaspora), *Kluyveromyces, Rhodotorula, Torulopsis, Zygosaccharomyces, Yarrowia,* and *Saccharomyces*.

In some embodiments, the microorganisms include *Escherichia coli, Klebsiella oxytoca, Zymomonas mobilis, Clostridium thermocellum, Pichia pastoris, Pichia stipites, Candida albicans, Saccharomyces cerevisiae, Phanerochaete chrysosporium Schizosaccharomyces pombe,* and/or *Yarrowia lipolytica.*

In some embodiments, the microorganism to be propagated includes genetically modified yeast such as genetically modified *Saccharomyces cerevisiae*. According to one embodiment, the yeast is a strain of *Saccharomyces cerevisiae* yeast. In some embodiments, the yeast is a strain of *Saccharomyces cerevisiae* capable of growing on glycerol. In other embodiments, the yeast is a genetically modified strain of *Saccharomyces cerevisiae* yeast capable of growing on glycerol. In still other embodiments, the yeast strain is a non-genetically modified strain (e.g. *Saccharomyces cerevisiae*).

As used herein, a "carbon source" refers to one or more compounds that include at least one carbon atom and can be used by a microorganism such as yeast to grow and/or reproduce to create additional biomass. Exemplary carbon sources include monosaccharides such as glucose, fructose, galactose, mannose, xylose and the like; disaccharides such as lactose, maltose, sucrose, cellobiose and the like; oligosaccharides; polysaccharides such as cellulose, hemicelluloses, starch, xylane and the like; single carbon substrates including only one carbon atom such as methanol; and polyols such as glycerol, but not limited thereto.

In some embodiments, the carbon source can be glycerol. Glycerol can be obtained from many different sources such as from a biodiesel industry and from an ethanol production process industry. The glycerol can be crude glycerol. Based on crude glycerol type used, both percentages and contaminant types may differ, and can include for example citric acid, sulphuric acid, methanol, fatty acid, ash, sodium acetate, soaps and salts derived from trans-esterification processes and the like. Crude glycerol can include various glycerol purities depending on the process used for biodiesel production. The glycerol can be from 55 to 99% pure, from 75 to 90% pure. Exemplary commercial sources of glycerol may be obtained from REG™ such as REG Glycerin-98 or REG Glycerin 80.

In some embodiments, the glycerol (e.g. crude glycerol) can be provided as part or all of the carbon source in an amount so as to help reproduce (propagate) a desired population of a microorganism (e.g., ethanologen) within a desired amount of time. In some embodiments, the carbon source consists essentially of glycerol. In some embodiments, the carbon source consists essentially of crude glycerol. In other embodiments, the carbon source consists of glycerol. In other embodiments, the carbon source consists of crude glycerol. In some embodiments, the glycerol (e.g. crude glycerol) is the entire carbon source, with no other carbon source such as glucose. In some embodiments, if a carbon source other than glycerol is present (e.g. glucose), it is present in an amount that does not result in the Crabtree effect. In some embodiments, the non-glycerol carbon source (e.g. glucose) amount that may be present does not exceed 5 grams per liter. In other embodiments, the non-glycerol carbon source (e.g. glucose) amount that may be present is 1 gram per liter or less, 0.5 grams per liter or less or 0.25 grams per liter or less. In some embodiments, the non-glycerol source is glucose and if present, may not exceed 5 grams per liter, or may be 1 gram per liter or less, 0.5 grams per liter or less or 0.25 grams per liter or less.

The glycerol provided can depend on factors such as the type and amount of other carbon sources present, the type and amount of nutrient source present, pH, temperature, desired time period for propagation, and the like. In some embodiments, the glycerol is provided in an amount less than or equal to 5% w/v in the composition (e.g. medium with a carbon and a nutrient source). In some embodiments, the glycerol is between 0.1 to 2% w/v of the composition. In still other embodiments, the glycerol can be as low as 0.2% w/v of the composition. In other embodiments, the glycerol is crude glycerol which is a by-product from a biodiesel production and can be provided in an amount less than or equal to 5% w/v in the composition. In some embodiments, the glycerol is provided in an amount less than or equal to 10% w/v in the composition (e.g. medium with a carbon and a nutrient source).

In some embodiments the glycerol provided is greater than 5 grams per liter. In some embodiments the glycerol provided is 3 to 100 g/L, or 5 to 100 g/L, or 5 to 50 grams per liter or 15 to 25 grams per liter. In some embodiments the glycerol is at least 5 g/L. In other embodiments, the glycerol is at least 3 g/L.

In addition to a carbon source, a nutrient source is also included to help propagate microorganisms such as ethanologens. As used herein, a "nutrient source" refers to one or more materials that can be used by a microorganism to grow and/or reproduce to create additional microorganisms and is different from a carbon source.

Figure 2:
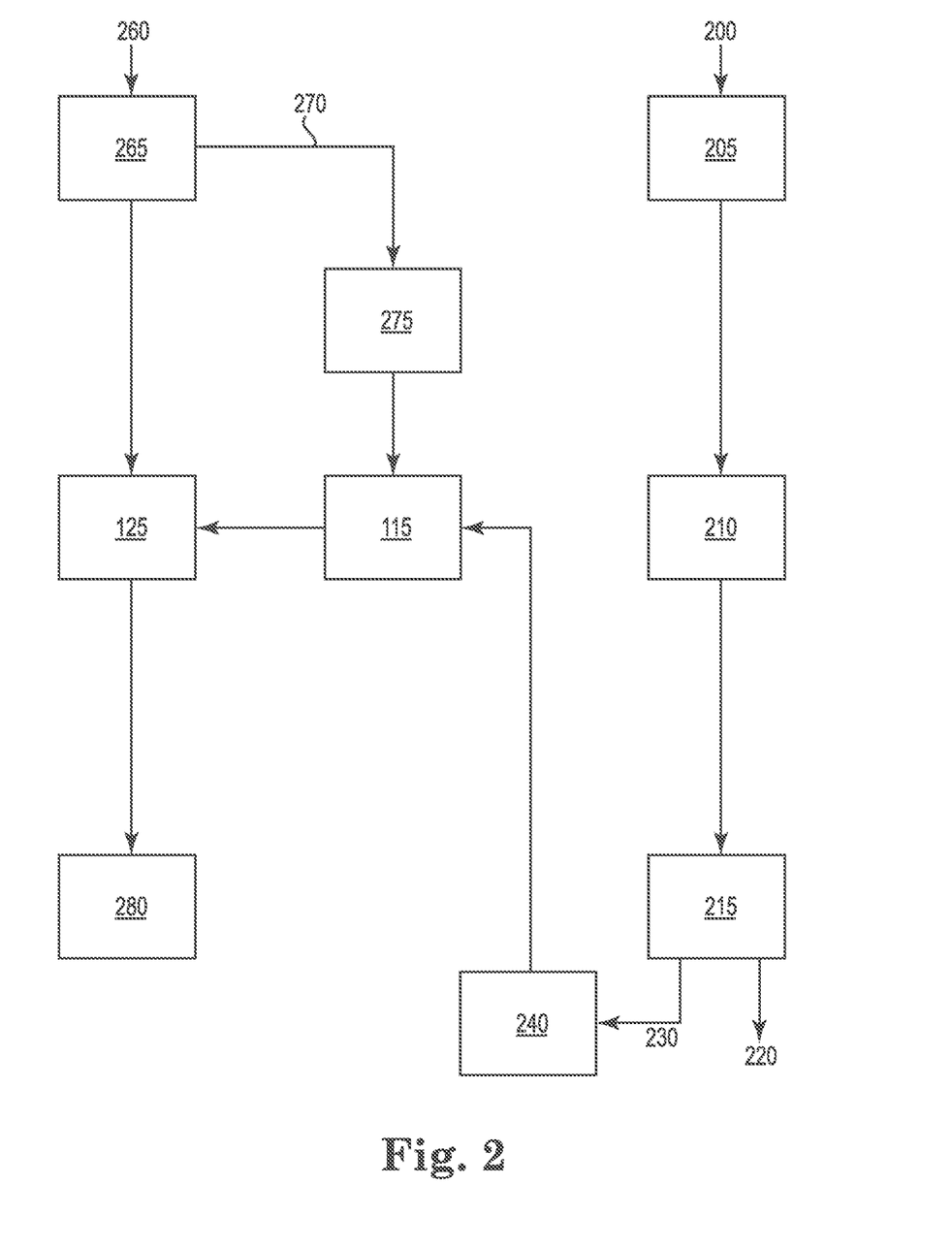
FIG. 2 shows a flow diagram of a propagation system according to an embodiment of the invention.

The nutrient source used includes a stillage component (e.g. whole stillage, thin stillage and/or syrup) Whole stillage is well-known and is a byproduct of distilling a fermentation product. For example, a well known process for making whole stillage is a corn grain-to-ethanol process and will be explained with respect to FIG. 2. As shown in FIG. 2, grain such as corn, barley, wheat, and/or sorghum 200 is prepared in system 205 so that it can be fermented in system 210 into a fermentation product that includes one or more biochemicals such as ethanol. Either the whole grain can be used or only one or more portions of the grain can be used. For example, system 205 may mill whole grains for fermentation or fractionate the grains into one or more separated portions before milling. After milling, the milled grain material can be further processed to break down polysaccharides and/or oligosaccharides into one or more monosaccharides such as glucose that can be fermented by, e.g., yeast. Methods of breaking down polysaccharides such as starch into glucose are well known and include e.g. hot water, such as hot water that includes an added acid such as sulfuric acid, and/or enzymatic pretreatment. After fermentation 210, the fermentation product is distilled in system 215, where the ethanol 220 is removed from the fermented mash in a distillation column. After the ethanol 220 is removed, the remaining residue is removed as stillage residue 230. The stillage residue 230 is known as "whole stillage." The whole stillage 230 can be optionally further processed via one or more systems 240 to further clarify or separate the whole stillage before being delivered to propagation system 115. For example, the whole stillage 230 can be subjected to a solid-liquid separation process to produce a solid stream of residue, also known as wet cake, and a liquid stream of residue, also referred to as thin stillage. The thin stillage can be further processed to increase the solids concentration by evaporation resulting in condensed distillers solubles or syrup. Typically the syrup is mixed back with the separated solid stream or wet cake and fed to a rotary drum dryer to remove the remaining moisture. The resulting dry solids are referred to as Dried Distillers Grains and Solubles or "DDGS", and can be sold as animal feed.

Such stillage component from the grain-to-ethanol producing process, including the whole stillage, wet cake, thin stillage, and/or syrup can be used as at least part of the nutrient source for propagating microorganisms such as yeast. Using at least a portion of the whole stillage provides an alternative or additional nutrient source as compared to, e.g., yeast extract. Using whole stillage (e.g. thin stillage) as the entire amount of nutrients or part of the nutrients can propagate yeast as well as, or better than, other nutrient sources such as yeast extract.

In some embodiments, the nutrient source includes a stillage component such as thin stillage, wetcake, syrup, and any combination thereof. The nutrient source can include syrup derived from thin stillage, thin stillage, or combinations thereof.

The stillage component can be provided in any amount so as to help reproduce (propagate) and generate a desired population of microorganism (e.g., ethanologen) within a given amount of time. The amount of stillage component provided can depend on factors such as the type and amount of other nutrient sources present, the type and amount of carbon sources present, pH, temperature, desired time period for propagation, and the like. In some embodiments, the nutrient source is provided only as a stillage component such as thin stillage.

In some embodiments, the nutrient source includes a stillage component derived from whole corn grain in an amount in the range of from 5 to 35 grams solids per liter of the composition (e.g. medium that includes a carbon and a nutrient source). In other embodiments, the nutrient source includes thin stillage derived from whole corn grain in an amount in the range of from 5 to 35 grams solids per liter of the composition. In some embodiments, the stillage component (e.g. thin stillage) contains less than 5000 mg/L of acetic acid, less than 8000 mg/L of lactic acid or both. In other embodiments, the nutrient source includes thin stillage but no yeast extract, urea or both. In some embodiments, the nutrient source is primarily thin stillage and if other nutrient sources such as yeast extract or urea are included, the other nutrient sources do not exceed 0.3 g/L In some embodiments, the nutrient source consists essentially of thin stillage, in other embodiments, the nutrient source consists of thin stillage. In some embodiments, the stillage component comprises, consists of or consists essentially of syrup.

Propagating a microorganism that can convert one or more monosaccharides into a biochemical will be described below by reference to an ethanologen such as a genetically modified yeast for making ethanol. The present disclosure, however, is not limited to propagating only such yeast and it should be understood that propagating any other microorganism (e.g. genetically modified or non-genetically modified) is contemplated.

As shown in FIG. 1, propagating an ethanologen includes combining at least the carbon source 105 and the nutrient source 110 to form a medium to facilitate growth of an sufficient amount of ethanologen (i.e. ethanologen cell mass) for inoculation (i.e. ethanologen inoculum to be supplied) to a fermentation system 125. The first cell mass of the microorganism (e.g., ethanologen) 100 can be included either while the medium is being formed, after the medium is formed, or both.

According to an exemplary embodiment the growth medium for the propagation system 115 includes water, a nutrient source 110 having whole stillage (e.g., thin stillage) as all or part of a nutrient source, a carbon source 105 including glycerol, and, optionally, one or more additional agents (not shown).

Optional additional agents for propagating yeast are well known and include, e.g., agents supplied with an ethanologen such as antibiotics, supplemental or accessory enzymes, materials for adjusting and maintaining pH, nutrients or other components providing nutritional or other benefits to the microorganism. Optional additional nutrients include, e.g., yeast extract, urea, diammonium phosphate, magnesium sulfate, zinc sulfate or other salts, and the like.

The ratio of nutrient source to carbon source is selected to grow a desired cell mass of microorganism such as a sufficient size cell mass of yeast for fermentation in a cellulosic ethanol process. Factors in selecting the ratio of nutrient source to carbon source include the type(s) and amount(s) of nutrient sources, the type(s) and amount(s) of carbon sources, types and amounts of additional growth medium agent(s), the types and initial amounts of microorganisms, the time period targeted for growing the microorganism, pH, temperature, and the like. Additional considerations include whether it is desired to condition the microorganisms during propagation to the environment expected during fermentation. Conditioning microorganisms to the fermentation environment can advantageously help the microorganisms operate (e.g., convert sugar to ethanol) more effectively.

In exemplary embodiments, the stillage component includes thin stillage and the weight ratio of glycerol to solids of thin stillage is in the range of from 0.05 to 20, from 0.1 to 10, from 0.2 to 5, and from 0.5 to 2.5.

Propagating the microorganism can begin when the microorganism is present in the growth medium and desired conditions are present. Conditions to consider for propagation of a microorganism include, e.g., amount of ingredients, pH, time period for growth of the microorganism, stir speed (if stirring is present), exposure to oxygen, temperature, and the like.

In some embodiments, the first cell mass (e.g., initial cell mass) of the microorganism is present in an amount less than 5 grams of ethanologens per liter of medium, less than 2 grams of ethanologens per liter of medium, or less than 0.5 grams of microorganism per liter of medium. In some embodiments, the first cell mass of the microorganism is from 0.5 to 1 grams of microorganism per liter of medium.

The cell mass can be propagated, depending on conditions, for a time to produce a desired cell mass. Typically, the desired cell mass is a size sufficient to ferment sugar into an alcohol (e.g., ethanol) within an economically desirable time period. Exemplary time periods include from 12-80 hours, 24-48 or 48-80 hours. In exemplary embodiments, the desired (e.g., second or final) cell mass of the microorganism (e.g. yeast) is present in an amount in the range of from 10 to 30 grams of microorganism per liter of medium. In some embodiments the second cell mass of the microorganism is in an amount in the range of from 10 to 30 grams of microorganism per liter of medium within a time period in the range of from 8 to 80 hours, wherein the time period begins when the first cell mass of the microorganism is combined with the carbon source and the nutrient source to propagate the first cell mass of the microorganism. The desired (e.g., second or final) cell mass of the microorganism is present in an amount in the range of from 1 to 20 grams of microorganism per liter of medium within a time period in the range of from 12 to 48 hours, wherein the time period begins when the first cell mass of the microorganism is combined with the carbon source and the nutrient source to propagate the first cell mass of the microorganism.

When grown on glycerol and stillage component, the yield of yeast cells can range from 0.5 grams to 30 grams per liter over a time period from 8-80 hours. In some embodiments, the rate of yeast growth (yeast cell mass productivity) can range from 0.1 gram/liter/hour to 0.5 gram/liter/hour or 0.2 gram/liter/hour to 0.4 gram/liter/hour.

According to embodiments where the microorganism includes yeast, the propagation system provides for the selective growth of yeast that can use glycerol as a carbon source (e.g., yeast that will propagate in a medium that includes glycerol) even if other yeast is present (e.g., as a contaminant); in a medium that provides glycerol as a sole carbon source (e.g., a medium that does not contain substantial amounts of glucose or other carbon sources), yeast that are capable of propagating using glycerol as a carbon source will propagate and other/contaminant yeast that may not be as capable of propagating using glycerol as a carbon source (such as more common forms of yeast that typically propagate in a medium containing glucose) will not propagate at the same rate (or at all).

The pH of the growth medium can be at a pH that helps reproduce (propagate) and generate a desired population of microorganism (e.g., ethanologen) within a desired amount of time. In some embodiments, the pH is between 4 and 8, preferably between 5 and 7, and even more preferably between 4.5 and 6. Techniques for adjusting and maintaining pH of a growth medium for propagating microorganisms such as an ethanologen are well known and include, e.g., adding one or more acidic materials and/or adding one or more basic materials.

The temperature of the growth medium can be at a temperature that helps reproduce (propagate) and generate a desired population of microorganism (e.g., ethanologen) within a desired amount of time. In some embodiments, the temperature is at a temperature in the range of from 15° C. to 50° C., preferably from 20° C. to 40° C., and even more preferably from 25° C. to 40° C.

Propagation of a microorganism can be performed according to a continuous process, fed-batch process, a batch process, or combinations thereof. Preferably, batch process has certain benefits associated therewith. In some embodiments, glycerol is provided in an amount as the carbon source such that the well-known "Crabtree effect" is not a concern so a batch process can be performed without producing an undue amount of ethanol. That is, in some embodiments relatively high levels of glycerol, unlike glucose, do not cause the propagation process to switch from a respirative pathway to an anaerobic pathway so as to generate ethanol instead of reproducing more microorganisms. A batch process can be highly desirable as it can be relatively easier to manage and control as compared to a continuous or fed-batch process.

In some embodiments, the growth medium is stirred for at least a portion of the propagation process so as to provide sufficient oxygen levels throughout the medium so as to promote aerobic respiration and, therefore, reproduction of the microorganism instead of, e.g., anaerobic fermentation production of ethanol. In some embodiments, if sufficient oxygen is not provided to the propagation medium, the process can switch to an anaerobic pathway and promote fermentation so as to produce alcohol to an undue degree.

According to exemplary embodiments where the microorganism includes yeast, to grow (inoculate) the yeast in the propagation system the temperature may be maintained in a range of about 28 to 32 degrees Celsius and the pH is in a range of about 5.2 to 5.8 for a time of at least 12 hours. For example, the yeast inoculum can be incubated under conditions including a temperature of about 30 degrees Celsius and a pH of about 5.5 for about 17 hours.

Also disclosed is a propagation system in which propagation can be performed in one or more stages. For example, where yeast is the microorganism to be propagated, the propagation system can include at least two stages. In a first stage, a yeast culture can be grown into an initial yeast inoculum. In the first propagation stage, the initial yeast inoculum is introduced into a vessel and diluted (e.g. by 250×). In the vessel, the initial yeast inoculum and a portion of the carbon source (e.g., glycerol), a portion of the nutrient source (e.g., thin stillage), and water may be supplied along with optional additional agents (discussed above). According to exemplary embodiments, the temperature may be maintained in a range of about 26 to 37 degrees Celsius and the pH in a range of about 3.5 to 6.5 for a time of at least 24 hours. For example, yeast can be grown in the first propagation stage under conditions including a temperature of about 30 degrees Celsius and a pH of about 5.5 for about 24 hours.

In the second propagation stage, the yeast inoculum from the first propagation stage is diluted (e.g. by 10×), typically after being transferred to another vessel. In the vessel, the yeast inoculum from the first propagation stage and a portion of the carbon source (e.g. liquid component including glycerol and/or other sugars), a portion of the nutrient source (e.g., thin stillage), and water may be supplied along with optional additional agents (discussed above). According to exemplary embodiments, the temperature may be maintained in a range of about 26 to 37 degrees Celsius and the pH in a range of about 3.5 to 6.5 for a time of at least 24 hours. For example, yeast can be grown in the second propagation stage under conditions comprising a temperature of about 30 Celsius and a pH of about 4.5 to about 5.5 for about 24 hours.

According to an embodiment, the yeast cell mass will grow by about 200 to 500 fold in the first stage and about 20 to 40 fold in the second stage.

After propagation, cell mass of microorganism is provided to a fermentation system such as system 125 so as to ferment a biomass such as pretreated lignocellulosic material and produce ethanol.

Example 1

Aerobic Propagation of Yeast, *Saccharomyces Cerevisiae*, Using Glycerol

Figure 3A:
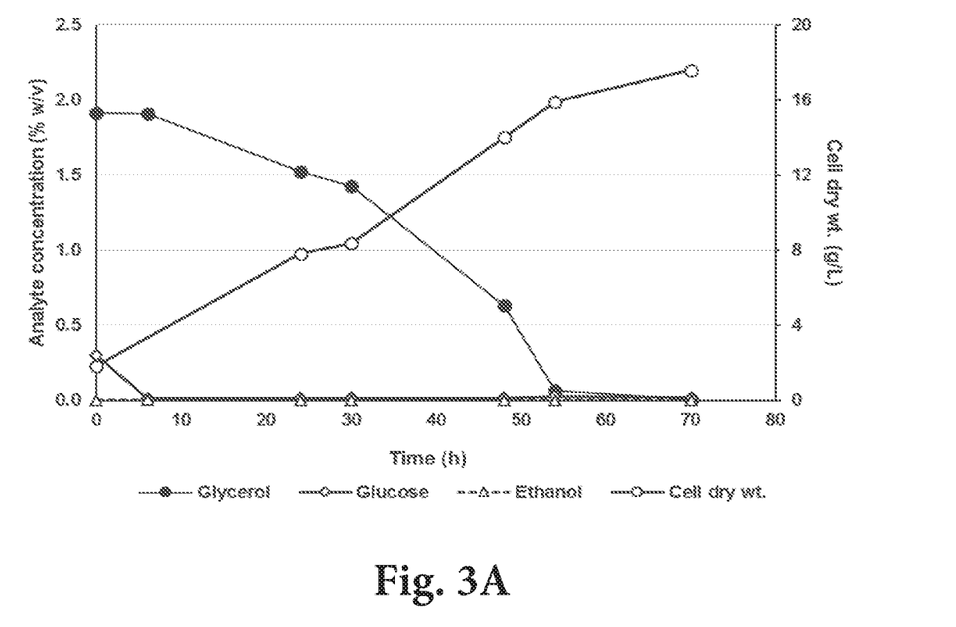
FIG. 3A shows aerobic yeast cell growth (in g/L) on glycerol and thin stillage according to one embodiment reported in Example 1.
Figure 3B:
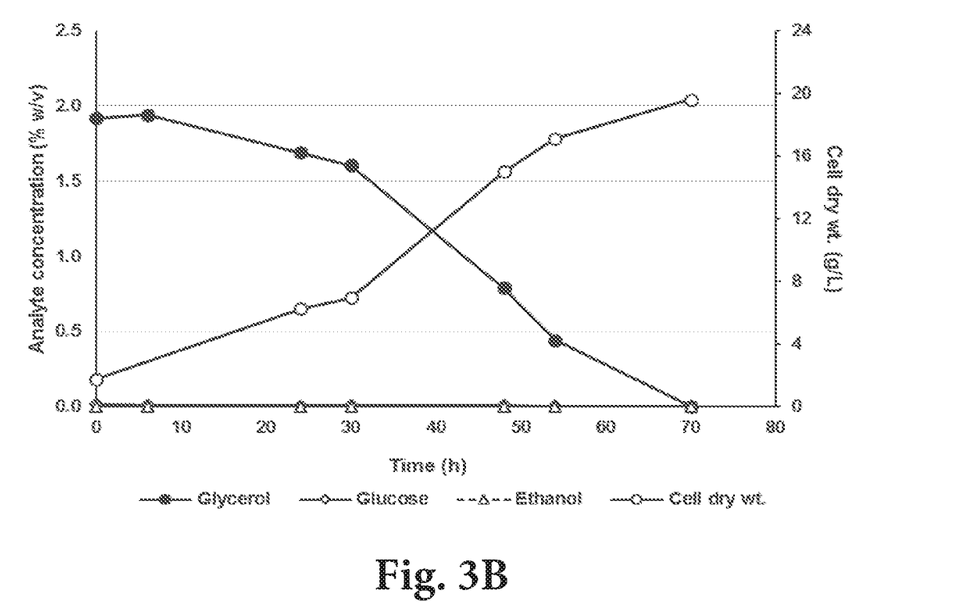
FIG. 3B shows aerobic yeast cell growth (in g/L) on glycerol and thin stillage according to one embodiment reported in Example 1.

The yeast *Saccharomyces cerevisiae* strain capable of growing on glycerol was used. The growth media used included glycerol, the byproduct from the biodiesel manufacturing process, purified to a technical grade, ~95% purity and clarified thin stillage, a byproduct from the starch to ethanol biorefinery. The liquid portion of the thin stillage in which most of the suspended solids are removed by centrifugation is termed clarified thin stillage. The media (1.5 L) was prepared in the 5 L reactors of the Bioflo310. Clarified thin stillage (CTS) was added to the reactor based on the total solids in the CTS. Target solids from the CTS were 20 g/L. The technical grade glycerol from biodiesel production was added to get to 1.5% w/v glycerol in the final mix. Urea was added at 0.24 g/L as an additional source of nitrogen. LACTOSIDE247™ was added at 5 ppm final concentration in the 1.5 L medium to prevent any bacterial contamination. Two reactors were prepared with exactly identical media in each. But, glucose was added to one of the reactors to a target initial concentration of 0.25% w/v. Although, the glycerol was targeted at 1.5% w/v, the final mix ended up at 1.9% w/v glycerol. This could likely have been due to some glycerol contributed by the thin stillage. Also, the glucose added to one of the reactors ended up being at a concentration of 0.3% w/v. The vessels were connected to the respective Bioflo310 units. The pH of the media in both the reactors was adjusted to 4.5 using sulfuric acid. Yeast, in active dry form (ADY) was used to inoculate each reactor at a dose of 1 g/L. The agitation was set at 750 rpm and the aeration was set at 1.5 SLPM (standard liters per minute) which will be equivalent to 1 vvm (volume of air per volume medium per min). The temperature was set at 31.1° C. (88° F.) for the entire duration of the propagation. Samples were withdrawn at regular intervals and analyzed by HPLC for glycerol, glucose, organic acids, and ethanol and cell dry weight. The results of glycerol, glucose, ethanol, and cell dry weight are shown in FIG. 3A (with additional glucose) & 3B (without additional glucose).

These results suggest that the yeast strain used grew well aerobically on glycerol as the major carbon source. Supplementation with additional glucose was not necessary. The cell mass produced at the end of propagation was 15.8 g/L and 17.8 g/L in media with and without additional glucose supplementation, respectively. The cell yield in media with no added glucose ended up at 0.9 g per g glycerol. The cell mass and yield produced without the addition of glucose was better than the media supplemented with glucose. In both cases, no ethanol production was observed. There is reduced or no Crabtree effect occurring when glycerol is used as the majority of the carbon source. During aerobic growth, the yeast also consumed more than 90% of the lactic (0.6 g/L starting lactic acid) and acetic acids e.g. 0.4 g/L starting acetic acid) brought into the medium by the clarified thin stillage.

Example 2

Figure 4A:
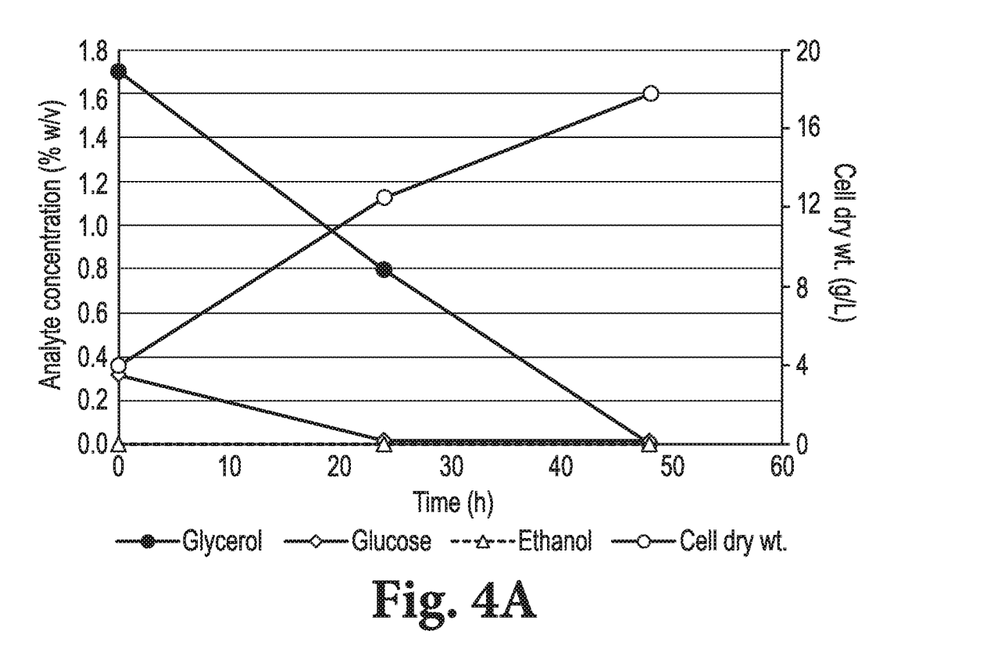
FIG. 4A shows aerobic yeast cell growth (in g/L) on glycerol and thin stillage according to one embodiment reported in Example 2.
Figure 4B:
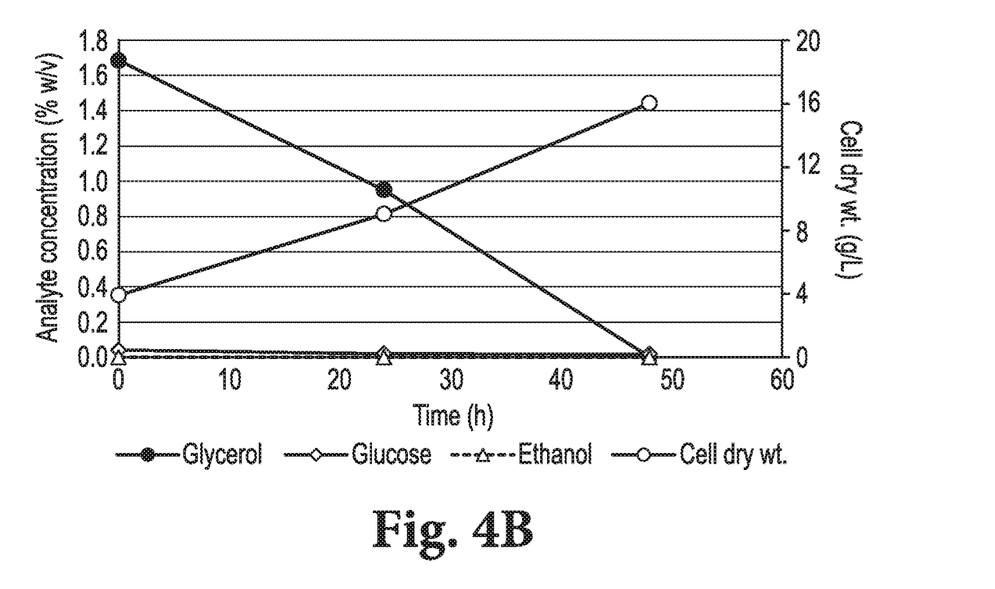
FIG. 4B shows aerobic yeast cell growth (in g/L) on glycerol and thin stillage according to one embodiment reported in Example 2.

*Saccharomyces cerevisiae* strain capable of growing on glycerol was used. The growth media in this study comprised of crude glycerol, the byproduct from the biodiesel manufacturing process, ~80% purity and thin stillage, a byproduct from the starch to ethanol biorefinery. The media (2.0 L) was prepared in the 5 L reactors of the Bioflo310. Thin stillage (TS) was added to the reactor based on the total solids in the stillage. Target solids from the TS was 20 g/L. The crude glycerol from biodiesel production was added to get to 1.5% w/v glycerol in the final mix. Urea was added at 0.24 g/L as an additional source of nitrogen. Lactoside247 was added at 5 ppm final concentration in the 2.0 L medium to prevent any bacterial contamination. Two reactors were prepared with exactly identical media in each. But, glucose was added to one of the reactors to a target initial concentration of 0.25% w/v. Although, the glycerol was targeted at 1.5% w/v, the final mix ended up at 1.7% w/v glycerol. This could likely have been due to some glycerol contributed by the thin stillage. Also, the glucose added to one of the reactors ended up being at a concentration of 0.3% w/v. The vessels were connected to the respective Bioflo310 units. The pH of the media in both the reactors was adjusted to 4.5 using sulfuric acid. Yeast, in active dry form (ADY) was used to inoculate each reactor at a dose of 1 g/L. The agitation was set at 750 rpm and the aeration was set at 2.0 SLPM (standard liters per minute) which will be equivalent to 1 vvm (volume of air per volume medium per min). The temperature was set at 31.1° C. (88° F.) for the entire duration of the propagation. Samples were withdrawn at regular intervals and analyzed for glycerol, glucose, organic acids, and ethanol and cell dry weight. The results of glycerol, glucose, ethanol, and cell dry weight are shown in FIG. 4A (with additional glucose) & 4B (without glucose).

These results suggest that the yeast strain used grew well aerobically on glycerol as the major carbon source, even if the glycerol from the biodiesel manufacturing was in its crude form prior to purification. Supplementation with additional glucose was not necessary even when the crude glycerol was used. The cell mass and yield produced without the addition of glucose was better than the media supplemented with glucose. The cell mass produced at the end of propagation was 12.1 g/L in media without additional glucose supplementation. The cell yield in this media ended up at 0.7 g per g glycerol. No ethanol production was observed in both cases. During aerobic growth the yeast also consumed more than 90% of the lactic and acetic acids brought in to the medium by the thin stillage.

Some additional non-limiting embodiments are provided below to further exemplify the present disclosure:

1. A method of propagating an organism, the method comprising:
   growing a first cell mass of the microorganism on a composition, the composition comprises a carbon source and a nutrient source, wherein the carbon source comprises glycerol and the nutrient source comprises a stillage component to propagate the first cell mass of the microorganism to form a second cell mass of the microorganism.

2. A method of propagating a microorganism comprising:
   (a) combining a composition with a first cell mass of a microorganism, the composition comprising:
   (i) a carbon source comprising glycerol; and
   (ii) a nutrient source comprising a stillage component; and (b) growing on the composition the first cell mass of the microorganism for a time period to form a second cell mass of the microorganism.

3. A system for propagating a microorganism comprising:
   (a) a propagation reactor vessel, wherein the propagation reactor vessel contains a composition comprising:
      (i) a carbon source comprising glycerol;
      (ii) a nutrient source comprising a stillage component; and
      (iii) a first cell mass of microorganism; wherein the microorganism can use the composition as a feed source and wherein the propagation reactor vessel is configured for growth of the first cell mass of microorganism to form a second cell mass of microorganism; and
   (b) an aerator coupled to the propagation reactor vessel.

4. The method or system as in any one of the preceding embodiments, wherein the carbon source consists essentially of glycerol and the nutrient source consists essentially of stillage.

5. The method or system as in any one of the preceding embodiments, wherein the carbon source consists of glycerol and the nutrient source consists of stillage.

6. The method or system as in any one of the preceding embodiments, wherein the carbon source consists essentially of glycerol.

7. The method or system as in any one of the preceding embodiments, wherein the carbon source consists of glycerol.

8. The method or system as in any one of the preceding embodiments, wherein the nutrient source consists essentially of a stillage component.

9. The method or system as in any one of the preceding embodiments, wherein the nutrient source consists of a stillage component.

10. The method or system as in any one of the preceding embodiments, wherein the glycerol is crude glycerol from a biodiesel production process.

11. The method or system as in any one of the preceding embodiments, wherein the crude glycerol is 75 to 90% pure.

12. The method or system as in any one of the preceding embodiments, wherein the glycerol is less than 5 percent w/v of the composition.

13. The method or system as in any one of the preceding embodiments, wherein the glycerol is greater than 5 g/L of the composition.

14. The method or system as in any one of the preceding embodiments, wherein the stillage component comprises a by-product of fermenting a grain material.

15. The method or system as in any one of the preceding embodiments, wherein the grain material comprises at least a portion of whole corn kernel material.

16. The method or system as in any one of the preceding embodiments, wherein the stillage component is provided in an amount in the range of from 5 to 35 grams solids per liter of the medium.

17. The method or system as in any one of the preceding embodiments, wherein the stillage component contains less than 5000 mg/L of acetic acid.

18. The method or system as in any one of the preceding embodiments, wherein the stillage component contains less than 8000 mg/L of lactic acid.

19. The method or system as in any one of the preceding embodiments, wherein the stillage component is thin stillage.

20. The method or system as in any one of the preceding embodiments, wherein the thin stillage contains less than 5000 mg/L of acetic acid.

21. The method or system as in any one of the preceding embodiments, wherein the thin stillage contains less than 8000 mg/L of lactic acid.

22 The method or system as in any one of the preceding embodiments, wherein the first cell mass of the microorganism is present in an amount less than 5 gram per liter of medium.

23. The method or system as in any one of the preceding embodiments, wherein the second cell mass of the microorganism is present in an amount in the range of from 10 to 30 grams per liter of medium.

24. The method or system of embodiment 1, wherein the growing is performed for a time period in the range from 12 to 24 hours.

25. The method or system as in any one of the preceding embodiments, wherein the growing is a batch or continuous process.

26. The method or system as in any one of the preceding embodiments, wherein the first cell mass of the microorganism is exposed to aerobic conditions during at least a portion of the time period.

27. The method or system as in any one of the preceding claim, wherein substantially no ethanol is produced by the first cell mass of the microorganism or second cell mass of the microorganism during the entire growing time period.

28. The method or system as in any one of the preceding embodiments, wherein the first cell mass of the microorganism comprises one or more ethanologens.

29. The method or system as in any one of the preceding embodiments, wherein the first cell mass of the microorganism comprises yeast.

30. The method or system as in any one of the preceding embodiments, wherein the yeast comprises genetically modified yeast.

31. The method or system as in any one of the preceding embodiments, wherein the yeast is selected from the group consisting of the genus, *Candida, Pichia, (Hansenula), Kloeckera (Hanseniaspora), Kluyveromyces, Rhodotorula, Torulopsis, Zygosaccharomyces, Yarrowia,* and *Saccharomyces.*

32. The method or system as in any one of the preceding embodiments, wherein the yeast is *Saccharomyces cerevisiae* species.

33 The method or system as in any one of the preceding embodiments, wherein the first cell mass of the microorganism comprises algae.

34 The method or system as in any one of the preceding embodiments, wherein the algae comprises the genus *Chlorella, Thraustochytriu, Schizochytrium* or *Crypthecodinium.*

What is claimed is:

1. A method of propagating a microorganism, the method comprising:
   (a) forming a propagation medium, wherein forming comprises combining glycerol and a stillage component, wherein the glycerol is in an amount of from 0.5 to 5 weight percent (wt/v) of the propagation medium, wherein the propagation medium comprises glucose in an amount of from 0 to 0.5 weight percent (wt/v), and wherein the stillage component is whole stillage, thin stillage, wet cake or combinations thereof; and
   (b) growing a first cell mass of the microorganism on the propagation medium to propagate the first cell mass of the microorganism to form a second cell mass of the microorganism.

2. The method of claim 1, wherein the glycerol comprises crude glycerol from a biodiesel production process.

3. The method of claim 1, wherein the glycerol comprises 75 to 90% pure glycerol.

4. The method of claim 1, wherein the stillage component comprises an amount from 5 to 35 grams solids per liter of the propagation medium.

5. The method of claim 1, wherein the stillage component is thin stillage.

6. The method of claim 5, wherein weight ratio of glycerol to solids of thin stillage is in the range of from 0.05 to 20.

7. The method of claim 1, wherein the first cell mass of the microorganism comprises an amount of cells less than 5 gram per liter of the propagation medium.

8. The method of claim 1, wherein the second cell mass of the microorganism comprises an amount of cells from 10 to 30 grams per liter of the propagation medium.

9. The method of claim 1, wherein the growing is by a batch, fed-batch or continuous process.

10. The method of claim 1, wherein substantially no ethanol is produced by the first cell mass of the microorganism or second cell mass of the microorganism during the growing for a time period.

11. A system for propagating a microorganism comprising:
  (a) a propagation reactor vessel, wherein the propagation reactor vessel contains a propagation medium comprising:
    (i) glycerol in an amount of from 0.5 to 5 weight percent (wt/v) of the propagation medium;
    (ii) a stillage component, wherein the stillage component comprises whole stillage, thin stillage, wet cake or combinations thereof; and glucose in an amount of from 0 to 0.5 weight percent (wt/v); and
    (iii) a first cell mass of microorganism; wherein the microorganism can use the propagation medium as a feed source and wherein the propagation reactor vessel is configured for growth of the first cell mass of microorganism to form a second cell mass of microorganism; and
  (b) an aerator coupled to the propagation reactor vessel.

* * * * *